United States Patent [19]

Dunn et al.

[11] Patent Number: 4,582,052
[45] Date of Patent: Apr. 15, 1986

[54] POVIDONE-IODINE DISPENSING FIBER

[75] Inventors: Richard L. Dunn, Birmingham; Danny H. Lewis, Gardendale, both of Ala.; Leonard E. Laufe, San Antonio, Tex.

[73] Assignee: Repromed, Inc., San Antonio, Tex.

[21] Appl. No.: 632,592

[22] Filed: Jul. 19, 1984

Related U.S. Application Data

[63] Continuation-in-part of Ser. No. 360,918, Mar. 23, 1982, abandoned.

[51] Int. Cl.⁴ .......................... A61B 5/00; A61K 9/22; A01N 25/34
[52] U.S. Cl. .................................... 128/130; 604/891; 604/892; 424/21; 424/22; 424/26; 525/937

[58] Field of Search ................. 128/130–138, 128/335; 604/890–897; 424/19–22, 8–12; 525/927

[56] References Cited

U.S. PATENT DOCUMENTS

| | | | |
|---|---|---|---|
| 3,896,819 | 7/1975 | Zaffaroni et al. | 128/130 |
| 3,921,636 | 11/1975 | Zaffaroni | 128/130 |
| 3,996,934 | 12/1976 | Zaffaroni | 128/130 |
| 4,014,987 | 3/1977 | Heller et al. | 128/130 |
| 4,024,871 | 5/1977 | Stephenson | 128/335.5 |

Primary Examiner—Thomas Wallen
Attorney, Agent, or Firm—B. B. Olive

[57] ABSTRACT

A fibrous article is formed of a polymer composition which incorporates povidone-iodine and provides for its sustained release.

13 Claims, 7 Drawing Figures

POVIDONE-IODINE DISPENSING FIBER

CROSS REFERENCE TO RELATED APPLICATION

This application is a continuation-in-part of applicants' copending patent application Ser. No. 360,918, filed Mar. 23, 1982, and entitled "Povidone-Iodine Dispensing Fiber"; now abandoned.

TECHNICAL FIELD

The invention relates to sustained release of a drug by means of a fibrous article containing the drug and adapted to be placed so as to treat a selected part of a living human or animal body.

BACKGROUND ART

The development of fibrous delivery systems for delivery of bioactive agents at controlled rates to specific body sites has been established for a variety of applications. However, each application presents unique problems both with respect to forming the fiber, combining the fiber with the agent whether in monolithic, coaxial or hollow fiber form and establishing those characteristics necessary to control release of the agent at some desired rate. While the desirable characteristics of povidone-iodine have been known for some time, the povidone-iodine complex had never to the best of applicant' knowledge been successfully incorporated into a fibrous delivery system prior to the invention described herein.

Povidone-iodine is a complex of poly(vinylpyrrolidone) and iodine. Poly(vinylpyrrolidone) (PVP) is produced by the free-radical polymerization of N-vinyl pyrrolidone. The polymer is water soluble even at high molecular weights and is physiologically acceptable to both animals and humans with uses as a plasma volume expander, drug vehicle, and as a suspending agent because of its protective colloid effect. Poly(vinylpyrrolidone) has also been added to fiber-forming polymers to give improvements in dye receptivity. Many of these polymer mixtures were melt spun.

Iodine is strongly complexed by PVP. Apparently, part of the iodine (about 30%) is converted to iodide which organically binds to the polymer. This bound iodide then stabilizes the remaining iodine in the same manner as potassium iodide in solution. The free iodine appears to be in solution in the PVP-iodide compound. In this complex, the vapor pressure of the free iodine is reduced essentially to zero resulting in a more stable microbiocide. The release of the available iodine at a slow rate from the complex when it is dissolved in water prolongs the microbiocidal action of the free iodine.

Iodine is recognized as a non-selective microbiocide which kills microorganisms immediately in tissue. Iodine has also been found to possess both fungicidal and viricidal properties. However, free iodine presents several difficulties in clinical use. The problems include oral toxicity, tissue irritation, and staining. The PVP-iodine complex minimizes most of these problems with reduced oral toxicity, almost no irritation to tissues, and no stains as a result of its water solubility.

Povidone-iodine has given excellent microbiocidal effects in surgical scrub, surgical preparation, and treatment of wounds, burns, and vaginal infections. Of particular interest, povidone-iodine is now frequently used as a douche or gel for treatment of vaginitis and vaginal trichomoniasis. In these applications, povidone-iodine affords several advantages in that it is non-staining, effective on a broad spectrum of bacteria, and does not appear to cause the formation of strain-resistant microorganisms as do the antibiotics. It would thus be desirable to incorporate povidone-iodine into a fiber.

As to other drug fiber technology, it will be noted that U.S. Pat. No. 3,926,188 to Baker et al discloses a polymeric drug dispenser which may be composed of polyethylene and may be inserted into body cavities, such as the vagina. U.S. Pat. No. 3,875,300 to Homm et al discloses intravaginal inserts which are composed of biodegradable polymers blended with medicaments in the form of fibers. U.S. Pat. No. 3,880,991 to Yolles is also noted as disclosing polymeric articles for dispensing drugs which may take the form of intrauterine devices. U.S. Pat. No. 3,991,766 to Schmitt et al and U.S. Pat. No. 4,118,470 to Casey et al are also noted as disclosing polymeric articles for dispensing drugs and formed into the shape of a thread, suture, ligature, or the like, for the controlled in vivo, continuous administration of a predetermined dosage of a drug to a living animal. U.S. Pat. No. 3,279,996 to Long, Jr. et al is noted as disclosing a drug enclosed in a silicone rubber capsule adapted for implantation and diffusion of the drug into the tissue of a living organism.

U.S. Pat. No. 3,896,819 to Zaffaroni teaches a drug dispensing device comprising a liquid mass of a low molecular weight drug compound enclosed by a wall. The Zaffaroni liquid reservoir system exhibits zero order release kinetics as contrasted to the first order or psuedo zero-order release kinetics of the present invention. Zaffaroni makes no reference to use of a high molecular weight polymer complex such as the povidone-iodine complex of the present invention. U.S. Pat. No. 3,921,636 to Zaffaroni teaches a drug dispensing device comprising a plurality of capsule like reservoirs containing drugs distributed through a matrix. The drug release rate from the reservoir walls is lower than that of the surrounding matrix material. Zaffaroni U.S. Pat. No. '636 also teaches forming the reservoirs in a matrix which assumes a fiber form. However, the Zaffaroni U.S. Pat. No. '636 system makes no reference to the use of or how to use the povidone-iodine complex of the present invention either in embedded reservoirs or otherwise. Also to be noted is U.S. Pat. No. 4,024,871 to Stephenson which teaches a multi-filament suture with several strands in which an antimicrobial is trapped within the interstices of the filaments without penetrating the fibers themselves.

With the above background art in mind, it is noted that the art has not disclosed povidone-iodine-loaded polymer fibers generally or specifically for intravaginal inserts. Neither has the art provided polyethylene fibers loaded with povidone-iodine and in a form adapted to provide a controlled, sustained release especially for intravaginal insert applications.

The general object of the invention is thus that of providing povidone-iodine loaded fibrous polymers specifically contemplated for use in the in vivo delivery of the povidone-iodine to humans and more specifically as an intravaginal implant. Even more specifically an object of the invention is to achieve this result with the fibrous polymer loaded with povidone-iodine in a thread-like form suited, for example, as the tail or pull string for an intrauterine device.

DISCLOSURE OF THE INVENTION

The invention is basically directed to providing both biodegradable and nonbiodegradable polymers in a thread-like form loaded with povidone-iodine complex by either dry or melt spinning. The fiber is monolithic in one form and in another form the fiber is coaxial in form with a coating effective to control the rate of delivery. In still another form, the fiber comprises a non-loaded fiber core provided with a sheath of polymer loaded with povidone-iodine complex. The fibers have been demonstrated to inhibit growth of a range of bacteria.

The invention recognizes that the previously-described properties of the povidone-iodine complex make it a good candidate for the control of venereal disease and pelvic inflammatory disease (PID) associated with intrauterine contraception. Normally, the uterine cavity is maintained in a bacteria-free state. It is suspected that the tail of an IUD placed in the uterus interferes with the protective mechanisms of the cervix and allows bacteria to ascend along the tail from the vagina. Consequently, an IUD tail with a slow release of an antimicrobial agent such as iodine would prevent bacteria migration through the cervix and significantly reduce the incidence of PID associated with the use of an IUD. The invention makes such an IUD practical.

The povidone-iodine complex according to the invention is incorporated into a fiber to give controlled release. Depending upon the application, either nonbiodegradable or biodegradable polymers may be used as the fiber matrix. Polyethylene and polypropylene are the preferred non-biodegradable polymers since they are biocompatible, they can be extruded at low melt temperatures, and they produce excellent fibers. For the biodegradable polymers, the invention prefers use of polycaprolactone, poly(DL-lactide), and poly(L-lactide). These polymers biodegrade within one to three years. Copolymers of these materials with glycolide degrade in shorter periods of time.

BEST MODE FOR CARRYING OUT THE INVENTION

Figure 1:
FIG. 1 is a cross-sectional view of monolithic, slow sustained release drug delivering fiber thread according to the invention.
Figure 2:
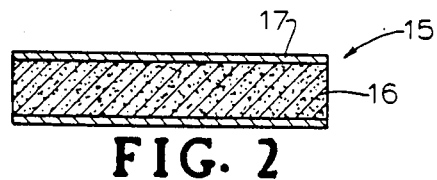
FIG. 2 is a cross-sectional view of a coated or coaxial-type slow sustained release drug delivery thread fiber according to the invention.
Figure 3:
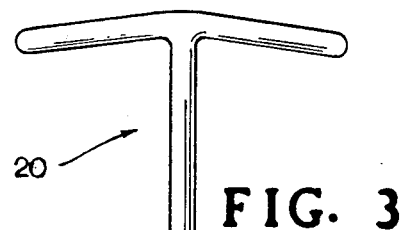
FIG. 3 is a side view of a popular type of intrauterine device illustrating use of the povidone-iodine loaded thread of the invention as the tail of the intrauterine device.

As previously mentioned, the fibrous delivery system of the invention is adapted in one embodiment to be formed as monolithic fiber such as the monolithic fiber 10 of FIG. 1. Also, the fibrous delivery system may be made in the form of a coaxial or coated-type fiber such as fiber 15 of FIG. 2 comprising the monolithic fiber 16 loaded with povidone-iodine complex and having an outer polymer coating 17 designed to control the release of the povidone-iodine complex. The fibrous delivery system according to the invention may also be in the form of a coaxial or core-type fiber such as fiber 25 in FIG. 7 comprising the monolithic fiber sheath 26 loaded with povidone-iodine complex and having an inner fiber core 27 which is not loaded with povidone-iodine complex but merely serves to provide integrity to fiber 25. In FIG. 3 the intrauterine device 20 is formed with the tail 21 made of a fiber loaded with povidone-iodine complex according to the invention.

Figure 7:
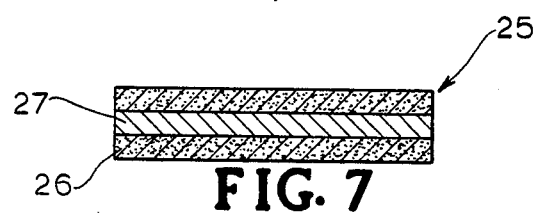
FIG. 7 is a cross-sectional view of an inner core or coaxial-type slow sustained release drug delivery thread fiber according to the invention.

Prior to the present invention, it was not known whether or not povidone-iodine could be incorporated into fibrous polymers, whether the release of the antimicrobial agent could be controlled and whether the iodine released from the fibrous system would still be effective against a variety of microorganisms. All of these desired results have in fact been achieved. To be noted here is that povidone-iodine complex has unique molecular characteristics, a relatively high melting point of 250° C., and solubility characteristics which could be expected to deter obtaining the desired release rate, mechanical strength and antimicrobial effects achieved by the invention. Of special interest to the present invention is that a sheath loaded composite fiber as illustrated in FIG. 7 has also been achieved.

Monolithic fibers formed from both biodegradable and non-biodegradable polymers have been loaded with povidone-iodine complex. Although two spinning methods, dry spinning and melt spinning were employed, the highest quality fibers were obtained by melt spinning the polymer blends. Satisfactory fibers were prepared from polycaprolactone and polypropylene with loadings of 25% of povidone-iodine. Samples of the monolithic fibers were then coated with a sheath of drug-free polycaprolactone to give fibers in which the initial release or burst of drug was diminished. This polymer sheath was applied by a solution-coating technique. Other samples may be prepared by spinning polymers loaded with povidone-iodine complex to provide a sheath around a central core of polymer which is not loaded with povidone-iodine complex.

The release rates of iodine from both the monolithic and coated fibers were determined in saline solution. The polycaprolactone monolithic fibers gave a quick release of iodine with a duration of several days. The polypropylene monolithic fibers and the coated fibers gave much slower release rates with an estimated duration of action greater than four weeks.

Representative samples of the fibers loaded with povidone-iodine and control fibers with no drug were evaluated for growth inhibition of five types of bacteria. Control fibers showed no inhibition of growth; whereas, the povidone-iodine fibers gave zones of inhibition which were dependent upon the quantity of iodine released.

Monolithic and reservoir fibers loaded with povidone-iodine (PI) were prepared according to the present invention. These fibers were then evaluated for mechanical properties, in vitro release rates, and activity against microorganisms. The details of examples of our procedures are next described.

PREPARATION OF MONOLITHIC FIBERS

Melt-spun monolithic fibers were prepared on a ram extruder. The most essential parts were a cylindrical, electrically-heated metal block, 4 inches in diameter and 8 inches long, with a 0.5 inch diameter bore through the center. A spinneret was fitted to the bottom of the block. A ram with a nominal diameter of 0.5 inch and driven by a variable speed motor was used to force the polymer through the spinneret. A pressure gauge located directed above the ram was used to measure the applied ram force. A take-up winder was located about 3 feet below the spinneret for collection of the fiber onto paper spools. In these procedures a single-orifice spinneret with a 0.020 inch orifice diameter and a 0.040 inch orifice length (2-to-1 length-to-diameter ratio) was used. In each example the polymer was charged to the barrel of the extruder, held there for 5 minutes to melt and reach an equilibrium temperature, and then forced through the spinneret and wound onto paper spools.

To obtain a more uniform blend of PI with the excipient polymer, the PI-polymer mixture was pelletized before spinning. The pelletizing equipment consisted of a 1.0 inch Killion extruder equipped with a rod die with a 0.25 inch diameter orifice, a 10 foot long quench trough filled with tap water at room temperature, a Killion film take-up roll, and a small Wiley mill. The extruded rod passed from the die through the water quench, through guides to the take-up rolls, and then through a tube to the Wiley mill where it was chopped into pellets about 0.13×0.13×0.06 inch in size.

The ram extruder was also used for dry spinning trials. A solution of PI and the excipient polymer was forced through a 6-mil single-orifice spinneret, and then through an electrically heated chamber that was 9 inches long and 2.5 inches inside diameter. The chamber was located about 4 inches below the spinneret surface. During the passage of the extrudate through the heated air chamber, the solvent evaporated and the fiber hardened.

Monolithic fibers were spun from both biodegradable and nonbiodegradable polymers containing povidone-iodine. A list of the fibers we successfully prepared is given in Table 1. Polycaprolactone was discovered to be a satisfactory and preferred biodegradable polymer excipient because of its ability to form strong fibers, its biocompatibility and its availability. Polypropylene and polyethylene were discovered to be satisfactory and preferred as nonbiodegradable polymer matrices because of their biocompatibility, ease of fiber formation, and availability.

TABLE I

MELT-SPINNING CONDITIONS FOR MONOLITHIC FIBERS CONTAINING 25% OF POVIDONE-IODINE

| Sample | Excipient Type | Polymer Source | Extrusion Conditions Temp., °C. | Rate, cm³/min |
|---|---|---|---|---|
| 1 | PCL | SORI | 220 | 1.14 |
| 2 | PCL | PCL-700 | 112 | 0.50 |
| 3 | PP | PROFAX | 240 | 1.15 |
| 4 | PP | MARLEX | 230 | 1.14 |
| 5 | PP | PROFAX | 220 | 1.13 |

Biodegradable Fibers

Using the procedures described earlier, we melt-spun biodegradable monolithic fibers of polycaprolactone (PCL) containing 25% by weight of povidone-iodine complex. The PI we used was a USP-grade powder supplied by Napp Chemical Company, Lodi, New Jersey. The free iodine content of the sample was reported as 10.81%. For the fibrous polymer, we used a high-molecular-weight PCL (inherent viscosity of 2.2 dl/g) prepared at Southern Research Institute (SORI). We mixed PCL and PI by dissolving them in a common solvent. Because of differences in the solubility parameters of the substances, we used a co-solvent system of dichloromethane and ethanol. Two solutions were prepared comprising PCL in dichloromethane and PI in ethanol. We then added the PI/ethanol solution dropwise to the PCL/dichloromethane solution. The resulting mixture was compatible and the combined solution was placed under a hood to allow the solvents to evaporate. The resulting film, containing 75% of PCL and 25% PI, was cut into small pieces and dried in a vacuum oven at 40° C. for 10 hours prior to melt spinning. The sample was spun as described earlier, and several yards of a strong, smooth fiber were collected (Sample 1).

To assess the spinnability of commercially available PCL, we used as another example medium molecular weight PCL 700 supplied by Union Carbide. A physical mixture of PCL 700 (ground in a Wiley mill) with PI powder was prepared to give a blend comprising 75/25 PCL/PI. This blend was then melt spun on the ram extruder by the procedures described earlier. The PCL 700/PI system spun well, and several hundred feet of fiber were collected (Sample 2).

NONBIODEGRADALE FIBERS

We next achieved the spinning of nonbiodegradable polymers with PI. We prepared physical mixtures of 75/25 polyolefin/PI from two commercial grades of polypropylene (PP). These mixtures were then melt-spun on the ram extruder. In each procedure we discovered that fiber quality was dependent on residence time and temperature in the ram extruder. A residence time greater than 15 minutes at or above 210° C. caused the mixture to separate and the povidone-iodine within the fiber to degrade. However, we were able to collect some loaded polypropylene fibers that were strong and uniform (Samples 3 and 4).

PREPARATION OF COAXIAL FIBERS

To obtain a constant rate of release of PI from fibers, a reservoir system was achieved in which PI located in the core of a fiber was surrounded by a sheath of a rate-controlling drug-free polymer. Both coaxial melt spinning and solution coating can be used to obtain these fibers.

In a typical melt-spinning procedure to produce coaxial fibers, the sheath material was dried and loaded into the barrel of a ram extruder heated to the proper extrusion temperature for that polymer. The agent, dissolved or dispersed in another more permeable polymer, was heated to the extrusion temperature in a separate chamber and delivered to a coaxial spinneret with a metering pump. The coaxial spinneret comprised two concentric rings. The molten sheath polymer was forced by pressure on the ram extruder through the outer ring of the spinneret. The agent/polymer core mixture was forced through the inner ring by the metering pump. Upon emerging from the spinneret, both materials solidified to form the coaxial fiber. The coaxial fiber having a drug-free polymer support core could also be produced on the coaxial spinneret by forcing the agent/polymer mixture through the outer ring and the agent-free polymer through the inner ring of the coaxial spinneret.

Coaxial fibers were also prepared by the coating of monolithic fibers. The sheath polymer was dissolved in a volatile solvent, and the solution was placed in the funnel end of a suitable gauge, e.g., 18 gauge, hypodermic needle. A short length of monolithic fiber was drawn through the polymer solution and the needle which acted as a die removed the excess solution. The procedure was repeated several times with sufficient time between coatings to allow the solvent to evaporate. The thickness of the sheath was controlled by the solids content of the coating solution and the number of applied coats. This process could also be used to prepare the coaxial fiber having a drug-free polymer core.

The method chosen for preparation of coaxial coated fibers was solution coating. Monolithic fibers of polypropylene and medium molecular weight polycaprolactone loaded with PI were drawn through a 30% solution of PCL in toluene by the needle procedure previously described. Satisfactory sheath thicknesses of polymer were obtained, and this method could be easily modified for production of larger quantities of fiber. A list of the coaxial fibers we successfully prepared is given in Table II.

TABLE II

SHEATH AND CORE DIMENSION OF COAXIAL FIBERS

| Sample | Core Material | Coating Material | Core Diameter, cm | Sheath Thickness, cm |
| --- | --- | --- | --- | --- |
| 6 | MARLEX-PP/PI 75/25 | SORI-PCL | 0.0509 | 0.0123 |
| 7 | PCL/700/PI 75/25 | SORI-PCL | 0.0345 | 0.0028 |
| 8 | PROFAX-PP/PI 75/25 | SORI-PCL | 0.0539 | 0.0086 |
| 9 | PCL-700/PI 75/25 | PCL-700 | 0.0345 | 0.0096 |

Mechanical Properties of Monolithic Fibers

The tensile properties of undrawn, melt-spun monolithic fibers were measured on a Model TMS Instron tester using a crosshead speed of 2 inches/minute and a guage length of 3 inches. The tensile properties of monolithic fibers loaded with PI are given in Table III. Since these fibers are undrawn, their strengths are expected to be quite low, which is shown by the low tenacity values. The tenacity of a fiber is the breaking strength in grams divided by the denier. Denier is a unit of measurement equal to the weight of 9000 meters of the fiber. These terms are those commonly used in the fiber and textile literature to describe the properties of fibers or yarns. A minimum fiber tenacity of 1.5 g/d is desirable for most textile fibers.

drawn or stretched to high ratios. The other fibers have useful but lower values of elongation and will break easily upon stretching. In addition, the higher values of initial modulus for the polypropylene indicate that they are stiffer than the PCL fibers. The tensile factor is the square root of elongation multiplied by tenacity, which normalizes the fiber strengths. The higher the tensile factor, the better the properties of the fiber.

The fibers in Table III do not have the highest desired strength. Nevertheless, the values indicate useful fibers and are encouraging since these fibers represent successful prototype devices without any attempts at optimization.

In Vitro Release of Fibers Loaded With Povidone-Iodine

For the determination of in vitro release rates of delivery systems, the proper receiving fluid for the agent and reliable method for analysis of the released agent must be chosen. Physiologic saline and phosphate-buffered saline have been used extensively to approximate body fluids in vitro. In our examples we chose to use phosphate-buffered saline. The pH of the receiving fluid was maintained at 7.5 to approximate that of cervical mucus. Sections of fibers containing PI were suspended in containers with the receiving fluid at 37° C. and the containers were agitated on a shaker bath. At specified time intervals, the fibers were withdrawn and placed into fresh receiving fluid. The used receiving fluid was held for analysis.

Figure 4:
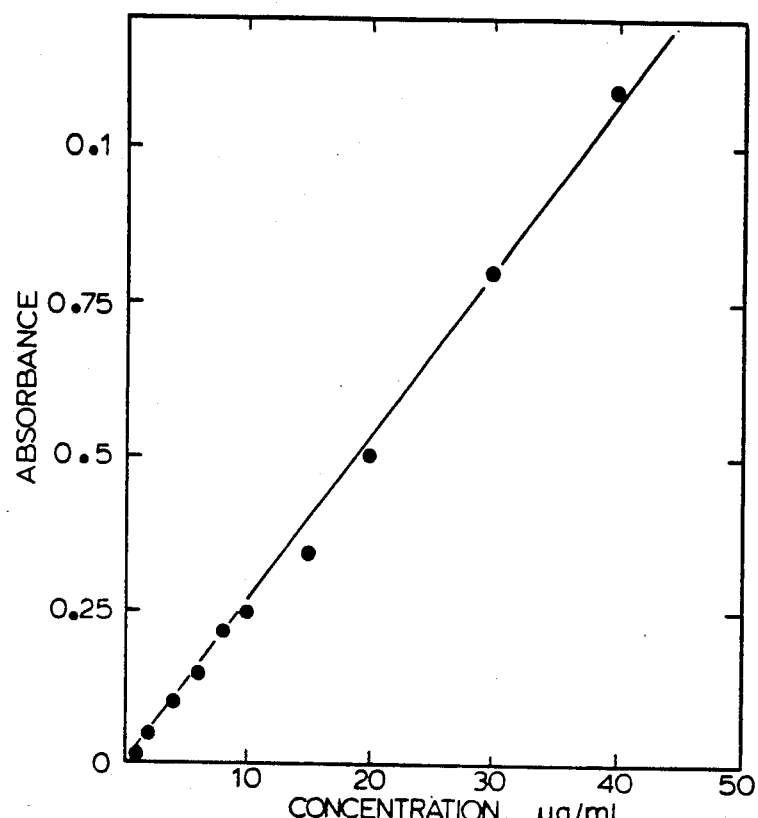
FIG. 4 is a Beer's law plot of povidone-iodine in phosphate-buffered saline.

In our release procedures, the receiving fluid contained PI at levels of about 30 ug/ml; therefore, standard iodometric titration procedures could not be used for determination of iodine. Spectrophotometric analysis methods were evaluated. A Beer's Law plot of PI concentration in saline solution versus absorbance was obtained at 207 nm. The correlation shown in FIG. 4 was satisfactory, and the receiving fluids from the in vitro procedures were evaluated by this spectrophotometric method for release of PI.

Figure 5:
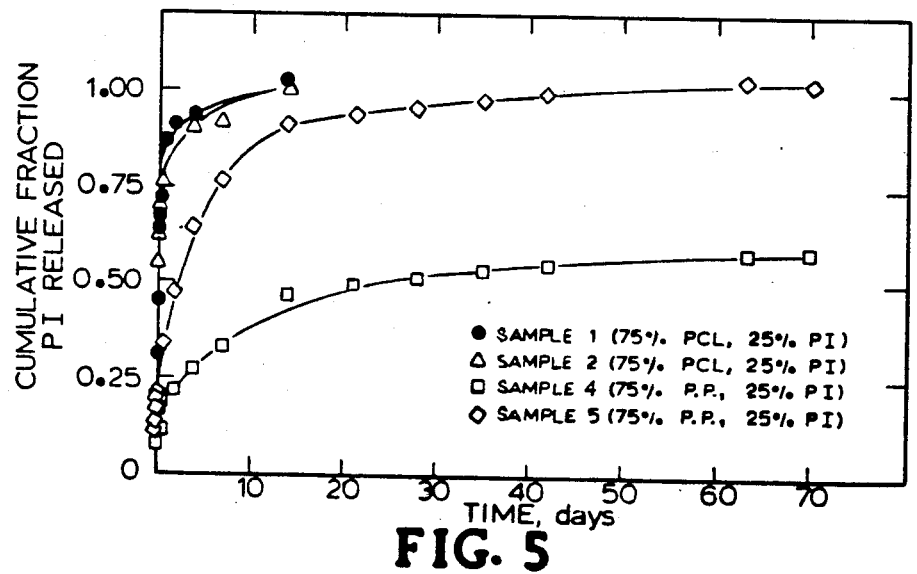
FIG. 5 is a plot illustrating release of povidone-iodine from monolithic fibers made according to the invention.

The data for the in vitro release of iodine from selected samples of monolithic fibers are given in FIG. 5 which shows the cumulative percentage release of PI based upon actual or theoretical drug loadings. Noticeably, polycaprolactone gives a fast release of PI which is almost exhausted after only one to two days.

Polypropylene is a more hydrophobic polymer, and it normally gives a slow release of water-soluble materials. In FIG. 5, the cumulative release of PI from monolithic fibers, indicates that PI is released at a very slow rate from PP. The duration of release will extend beyond four weeks for one fiber specimen. The sample releasing longest, i.e., Sample 4, was produced from Marlex HGN-020-01 (Phillips 66) a high- molecular-weight polymer (approximately 400,000). Sample 5

TABLE III

| | TENSILE PROPERTIES OF MONOLITHIC FIBERS | | | | | |
| --- | --- | --- | --- | --- | --- | --- |
| Sample | Composition with 25% Povidone-Iodine | Fiber Diameter, m | Initial Modulus g/d | Elongation at Break (E), % | Tenacity (T), g/d | Tensile Factor [√E(T)] |
| 1 | SORI - PLL | 132 | 3.9 | 5.3 | 0.09 | 0.21 |
| 2 | PCL - 700 | 119 | 4.9 | 483.2 | 0.13 | 2.86 |
| 3 | PROFAX PP | 183 | 10.3 | 3.0 | 0.25 | 0.43 |
| 4 | MARLEX PP | 191 | 11.4 | 3.3 | 0.27 | 0.49 |

Of the fibers given in Table III, the medium molecular weight PCL/PI fiber has the best properties. The high value of elongation indicates that this fiber can be which used the Hercules polypropylene (Profax 6323) had a weight-average molecular weight of only about 100,000. The higher molecular weight and crystallinity of the Marlex HGN polymer decreased the permeation of drug from within the monolithic matrix.

Figure 6:
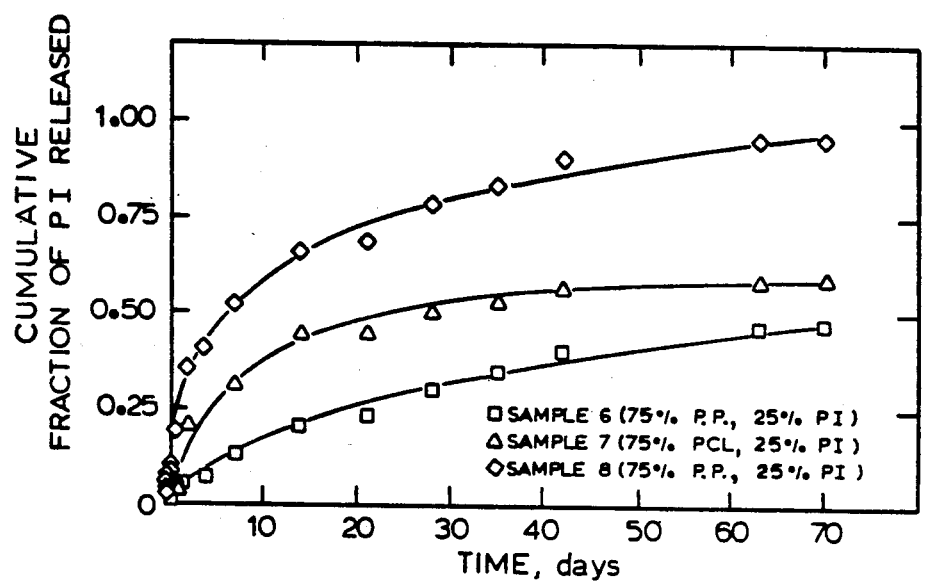
FIG. 6 is a plot illustrating release of povidone-iodine from coaxial coated fibers made according to the invention.

The coaxial fibers coated with a drug-free polymer membrane had less of an initial burst of PI. This effect is seen in FIG. 6 which shows the cumulative percentage release of PI based upon the theoretical drug loading. Thus, a coating of PCL which was discovered to be quite permeable to PI in the monolithic fibers slows down the release rate considerably for both PCL and PP monolithic fibers. These results indicate that both biodegradable and nonbiodegradable fibers can be prepared that will exhibit a long duration of action.

The release rates with the coaxial fibers coated with a drug-free polymer are most encouraging since it might have been anticipated that a coating of any high-molecular-weight polymer could completely stop the release of povidone and its complexed iodine. This suspicion was based upon the hypothesis that high-molecular-weight water-soluble polymers such as povidone would not permeate high-molecular-weight hydrophobic polymers. Apparently, either there is permeation of the PCL sheath membrane by povidone or the PCL membrane contains pores through which the povidone-iodine complex can migrate.

The coaxial core fibers having a drug-free polymer core would behave more nearly like the monolithic fibers illustrated in FIG. 6.

Evaluation of Antimicrobial Effects

Fibers containing the PI complex were tested for antimicrobial activity against three bacteria and one yeast. Fibers, approximately 0.5 centimeter in length, were placed on the surface of primary test plates (duplicate plates of Tryptic-Soy Agar medium seeded with each test microorganism). The plates were incubated at 35° C. for eighteen hours, and zones of growth inhibition were measured. The fibers were removed from the test plates and transferred to plates of 1.5% Bacto-Agar in water; these plates were incubated in a humidified chamber at 35° C. for two weeks. Following the two-week incubation, the fibers were transferred to secondary test plates (prepared in the same manner as the primary test plates). The secondary test plates were incubated at 35° C. for eighteen hours and observed for zones of growth inhibition.

Any time a drug is incorporated into a controlled-release device, the activity of the drug must be assayed to determine whether the drug has been altered by fabrication procedures. In this study, a simple growth-inhibition test with the loaded fibers on cultured agar plates was deemed satisfactory to demonstrate antimicrobial activity.

The results of our growth-inhibition tests are given in Table IV. The control fibers of PCL and PP showed no inhibition of growth of the four microorganisms given in Table IV. The medium molecular weight PCL monolithic fiber loaded with PI gave a wide zone of inhibition against all four microorganisms. Since the diameter of the fiber used in this test was only 0.119 mm, a zone of inhibition of 2.2 to 5.2 mm is quite large and shows the high rate of release of PI.

TABLE IV
ANTIMICROBIAL ACTIVITY OF FIBERS ON PRIMARY TEST PLATES

| Fiber | | Width of Inhibition Area[1], mm Microorganisms | | | |
|---|---|---|---|---|---|
| Sample | Description | Staphylococcus aureus | Streptococcus faecium | Escherichia coli | Candida albicans |
| 2 | PCL, 75%; PI, 25% | 5.2 | 4.4 | 2.4 | 2.2 |
| 5 | P.P 75%; PI, 25% | 1.6 | 1.5 | 0 | 0 |
| 9 | Core: PCL, 75%; PI, 25% Sheath: PCL | 0 | 0 | 0 | 0 |
| 10 | PCL (Control for Sample 2) | 0 | 0 | 0 | 0 |
| 11 | P.P. (Control for Sample 5) | 0 | 0 | 0 | 0 |

[1]Inhibition is measured perpendicular to the fiber at the greatest width of inhibition. Each width reported is the average of two measurements.

In another significant test, Neisseria gonorrhoeae ATCC 19424 was inhibited by the povidone-iodine impregnated fiber Sample 2. Neisseria gonorrhoeae was spread on the surface of solid medium (GC Agar Base [BBL 11275] supplemented with 1% hemoglobin [BBL 11871] and 1% (v/v Iso VitaleX TM Enrichment [BBL 11875].) in Petri plates; approximately 7 mm lengths of fiber Sample 2 were placed on the inoculated medium. The test plates were incubated in a candle jar at 37C for 18 hours. The greatest width of the inhibition zone perpendicular to the fiber was measured. The mean width of eight inhibition zones was 3.21 mm (range: 2.72–3.70 mm).

The PP monolithic fiber was effective against only two of the microorganisms. This result was expected since the release of PI from this fiber was considerably less than that from the PCL monolithic fiber.

The coaxial coated fiber of PCL/PI coated with additional PCL gave no inhibition of growth. This result was also expected since all of these coaxial fibers gave very slow rates of release of PI.

It is believed that the coaxial core fiber of PCL coated with PCL/PI would be effective against all four of the microorganisms in view of the performance of Sample 2.

The data given in Table IV are for the primary test plates. Tests on the secondary plates followed a two-week incubation of the fibers on bacteria-free agar plates showed that none of the fibers gave a zone of growth inhibition. These results were expected since our in vitro release data had indicated that the PCL/PI monolithic fiber and coaxial core fiber were almost depleted of drug in about two days. Since these fibers gave a wide zone of inhibition on the primary plates, their supply of PI would have been exhausted after two weeks and no antimicrobial activity would be expected.

All of the other fibers including the PP monolithic fiber and the PCL/PI coaxial coated fiber would still be releasing PI after two weeks but at such a low rate that areas of inhibition would not have been detected. Nevertheless, while more complex tests might be devised, these agar-plate tests did demonstrate the continued antimicrobial action of PI incorporated into and released from the fibrous systems. They also demonstrated that povidine-iodine, an effective anti-microbial agent, can be successfully incorporated into fibrous polymers which are either biodegradable or nonbiodegradable. Both monolithic and coaxial fibers can be prepared to provide controlled delivery of the povidone-iodine. Further, these fibers can be made to exhibit either fast release rates with short durations of action, or slow release of the drug with prolonged activity greater than four weeks. Povidone-iodine when released from the fibrous systems can thus be made effective against a variety of microorganisms such as those described by way of example as well as other bacteria and virus commonly encountered in the body and particularly in the vagina for which the invention fibers are particularly intended.

We claim:

1. An intrauterine device having a tail thread, said tail thread comprising a polymeric-formed fiber for controllably dispensing povidone-iodine complex in which said fiber comprises a molded thread-like polymeric structure incorporating said povidone-iodine complex in a form adapted for sustained slow release therefrom.

2. A device as claimed in claim 1 wherein said polymeric-formed fiber is in monolithic form and in which said complex is dispersed in a polymer establishing said form.

3. A device as claimed in claim 2 wherein said polymer is selected from the group consisting of polyethylene, polypropylene, polycaprolactone, poly(Dl-lactide), and poly(L-lactide).

4. A device as claimed in claim 1 wherein said polymeric-formed fiber is in coaxial form and said complex is dispersed in one polymer establishing said form and is surrounded by another polymer establishing the rate of release therefrom.

5. A device as claimed in claim 4 wherein said one polymer is selected from the group consisting of polyethylene, polypropylene, polycaprolactone, poly(Dl-lactide), and poly(L-lactide).

6. A device as claimed in claim 1 wherein said polymeric-formed fiber is in coaxial form and one polymer forms a core and is surrounded by another polymer having said complex dispersed therein which forms a sheath around the core.

7. A device as claimed in claim 6 wherein said another polymer is selected from the group consisting of polyethylene, polypropylene, polycaprolactone, poly(Dl-lactide), and poly(L-lactide).

8. A device as claimed in claim 4 wherein said another polymer is nylon.

9. A device as claimed in claim 4 wherein said another polymer is polyester.

10. A device as claimed in claim 1 wherein said polymeric-structure incorporating said povidone-iodine is formed from a polymer selected from the group consisting of polyethylene, polypropylene, polycaprolactone, poly(Dl-lactide), and poly(L-lactide).

11. A device as claimed in claim 1 wherein said polymeric-formed fiber is in coaxial form and said complex is dispersed in one polymer establishing said form and is surrounded by the same said one polymer free of said complex and controlling the rate of release thereof.

12. An intrauterine device having a tail thread and said tail thread comprising a polymeric-formed fiber for controllably dispensing povidone-iodine complex in which said fiber comprises a molded thread-like monolithic solidified polymeric structure formed from a mixture of povidone-iodine complex and a polymer permeable to and having a melting point below the melting point of said povidone-iodine complex and having a molecular weight sufficiently high after said polymer and povidone-iodine complex are mixed, molded and solidified to maintain structural integrity in a solidified thread-like form and incorporating said povidone-iodine complex dispersed in said polymer after being molded in said solidified thread-like non-reservoired form and being adapted for sustained slow release therefrom.

13. A drug-dispensing tail thread in combination with an intrauterine implant, said thread comprising a polymeric-formed fiber for controllably dispensing povidone-iodine complex in which said fiber comprises a molded thread-like monolithic solidified polymeric structure formed from a mixture of a water soluble povidone-iodine complex having iodine organically bound to a polymer and a polymer permeable to and having a melting point below the melting point of said povidone-iodine complex and having a molecular weight sufficiently high after said polymer and povidone-iodine complex are mixed, molded and solidified to maintain structural integrity in a solidified thread-like form and incorporating said povidone-iodine complex dispersed in said polymer after being molded in said solidified thread-like form and being adapted for sustained slow release therefrom according to first order or pseudo zero-order kinetics.

* * * * *